United States Patent
Westernacher et al.

(10) Patent No.: US 6,268,538 B1
(45) Date of Patent: Jul. 31, 2001

(54) METHOD FOR PRODUCING AND PURIFYING 3-(4-HYDROXYPHENYL)-1,1,3-TRIMETHYLINDAN-5-OL

(75) Inventors: Stefan Westernacher, Seabrook, TX (US); Claudia Laukötter, Willich (DE); Jürgen Stebani, Kaufbeuren (DE); Gerhard Fennhoff, Willich (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/446,563

(22) PCT Filed: Jun. 22, 1998

(86) PCT No.: PCT/EP98/03802

§ 371 Date: Jan. 24, 2000

§ 102(e) Date: Jan. 24, 2000

(87) PCT Pub. No.: WO99/01413

PCT Pub. Date: Jan. 14, 1999

(51) Int. Cl.$^7$ ................................................ C07C 39/12
(52) U.S. Cl. ................................................ 568/734
(58) Field of Search ................................. 568/734

(56) References Cited

U.S. PATENT DOCUMENTS

| | | | |
|---|---|---|---|
| 2,754,285 | 7/1956 | Petropoulos | 260/47 |
| 2,819,249 | 1/1958 | Petropoulos et al. | 260/45.95 |
| 2,979,534 | 4/1961 | Petropoulos et al. | 260/619 |
| 3,264,357 | 8/1966 | Webb et al. | 260/619 |
| 3,264,358 | 8/1966 | Webb et al. | 260/619 |
| 3,271,463 | 9/1966 | Howard | 260/619 |
| 4,201,877 | 5/1980 | Yamazaki et al. | 568/720 |
| 4,366,328 | * 12/1982 | Numata | 568/734 |

FOREIGN PATENT DOCUMENTS

| | | |
|---|---|---|
| 5-294879 | 11/1993 | (JP) . |
| 60-35150 | 2/1994 | (JP) . |

* cited by examiner

*Primary Examiner*—Michael L. Shippen
(74) *Attorney, Agent, or Firm*—Joseph C. Gil; Aron Preis

(57) ABSTRACT

A process is disclosed for the preparation and purification of 3-(4-hydroxyphenyl)-1,1,3-trimethylindan-5-ol. Accordingly, isopropenylphenol, its dimers or oligomers undergo isomerization in the presence of an acid catalyst, crude 3-(4-hydroxyphenyl)-1,1,3-trimethylindan-5-ol is isolated from the reaction mixture and purified by distillation.

4 Claims, No Drawings

METHOD FOR PRODUCING AND PURIFYING 3-(4-HYDROXYPHENYL)-1, 1,3-TRIMETHYLINDAN-5-OL

The present invention relates to a process for the preparation and purification of 3-(4-hydroxyphenyl)-1, 1,3-trimethylindan-5-ol by isomerisation of isopropenylphenol, its dimers or oligomers, separation of 3-(4-hydroxyphenyl)-1,1,3-trimethylindan-5-ol and subsequent distillation of the crude product.

Various processes for preparing 3-(4-hydroxyphenyl)-1,1,3-trimethylindan-5-ol, referred to below as bisphenol indane, are already known.

Thus U.S. Pat. No. 2,754,285 and U.S. Pat. No. 2,819,249 disclose a preparative route to indanes via the acid-catalysed dimerisation of α-methylstyrene. The indanes are subsequently sulphonated and then saponified with potassium hydroxide.

U.S. Pat. No. 2,979,534 discloses that the monomeric isopropenylphenols obtained by decomposition of bisphenols can be dimerised in the presence of aromatic sulphonic acids or mineral acids at temperatures of 110 to 160° C. to form bisphenol indane. The decomposition of bisphenol and formation of indane may also be carried out in one step. A product of low purity, which even after recrystallisation from benzene/cyclohexane had a melting point of only 165–166° C., was obtained by this process.

U.S. Pat. No. 3,264,357 discloses the preparation of bisphenols by the reaction of a mixture of two isomeric forms of the dimeric isopropenylphenol with phenols in the presence of strong acids. It is reported that, in the absence of reactive phenols, bisphenol indane is formed at a reaction temperature of 90° C. According to U.S. Pat. No. 3,264,358, bisphenol indane can be obtained by the reaction of a mixture of the two isomeric forms of the dimeric isopropenylphenol with strongly acid catalysts, for example, by tempering for two hours in boiling concentrated hydrochloric acid.

U.S. Pat. No. 3,288,864 discloses the preparation of bisphenol indane by self-condensation of monomeric isopropenylphenol in the presence of Friedel-Crafts catalysts at temperatures of from 50 to 150° C. and JP-A 60/35150 discloses the isomerisation of isopropenylphenol or of its oligomers in the presence of solid catalysts such as aluminum oxide or terra alba.

According to U.S. Pat. No. 4,334,106, bisphenol indane can be prepared by the reaction of isopropenylphenol or its oligomers in halogenated carboxylic acids or formic acid at temperatures of from 0 to 90° C.

According to JP-A 5/294879, bisphenol indane can be obtained by thermal decomposition of bisphenol A in the presence of activated clay and U.S. Pat. No. 3,271,463 discloses the formation of bisphenol indane as a by-product during the treatment of bisphenol A with aqueous sulphuric acid at 90 to 150° C. During both processes relatively large quantities of spirobisindane bisphenol are formed and this has to be separated from aromatic hydrocarbons by recrystallisation.

The processes described are in many cases still unsatisfactory for an industrial production of bisphenol indane for use as starting material for the production of plastics. An expensive purification by recrystallisation is necessary in order to obtain bisphenol indane in the purity required for this purpose. A process which can be carried out without a recrystallisation step has now been found.

This invention provides a process for the preparation and purification of bisphenol indane, wherein isopropenylphenol, its dimers or oligomers or mixtures thereof are isomerised in the presence of an acid catalyst, crude bisphenol indane is isolated from the reaction mixture and this crude product is purified by distillation under reduced pressure.

Isopropenylphenol or its dimers or oligomers are used as starting materials for the process according to the invention. These are easily accessible and can be prepared, for example, by the methods described in U.S. Pat. No. 3,288,864 or U.S. Pat. No. 4,201,877.

The isomerisation is preferably carried out in the presence of a solvent. A large number of different solvents are suitable for use as the solvent. Examples are hydrocarbons such as petroleum ether, cyclohexane, benzene, toluene or xylene, alcohols such as methanol, n-propanol or n-butanol, carboxylic acids such as formic acid or acetic acid, propionic acid, halogenated carboxylic acids such as trichloroacetic acid or trifluoroacetic acid, chlorinated hydrocarbons such as methylene chloride, chloroform, trichloroethylene or carbon tetrachloride, substituted aromatics such as chlorobenzene or nitrobenzene; dimethyl sulphoxide, dimethylformamide, dimethylacetamide or N-methylpyrrolidone are also suitable. Preferably chlorobenzene is used. The quantity of solvent is preferably two to three times the quantity of isopropenylphenol used.

The isomerisation reaction is carried out in the presence of an acid catalyst. Brønsted acids or Lewis acids may be used as catalysts for the process according to the invention. Examples are mineral acids such as hydrochloric acid or sulphuric acid, organic acids such as sulphonic acids or halogenated carboxylic acids, boron trifluoride and metal halides such as $AlCl_3$, $FeCl_3$ or $ZnCl_2$. Besides these heterogeneous catalyst systems may also be used, for example, in the form of a fixed bed. Examples are acidic ion-exchange resins, zeolites, oxides or hydroxides or mixed oxides of transition metals or of rare earths, heteropolyacids, $Al_2O_3$, $SiO_2$ and mixtures thereof. Preferably Lewis acids and particularly preferably boron trifluoride are used as catalysts. In a preferred embodiment of the process the catalyst is added, optionally in portions, in a quantity of from 0.002 to 5 wt. %, preferably from 0.3 to 0.5 wt. %, based on the quantity of isopropenylphenol used, to the reaction mixture after heating to a temperature within the range of 60 to 110° C., preferably 70 to 90° C.

The isomerisation is carried out preferably at a temperature within the range of 0 to 160° C., particularly preferably at a temperature within the range of 110 to 150° C. and most preferably at 130 to 140° C. The reaction is allowed to take place for 1 to 600 minutes, particularly preferably for 2 to 60 minutes.

In a preferred embodiment, subsequent to the isomerisation reaction the reaction mixture is neutralised by the addition of a base. The neutralisation is carried out preferably at a temperature within the range of 60 to 100° C., particularly preferably at 70 to 90° C. A large number of different bases or their mixtures are suitable for the neutralisation. Examples are metal hydroxides such as NaOH, KOH, $Mg(OH)_2$, $Ca(OH)_2$, alcoholates such as sodium methylate, sodium ethylate, sodium phenylate, potassium methylate, potassium ethylate, potassium phenylate, magnesium methylate, magnesium ethylate, magnesium phenylate, calcium methylate, calcium ethylate, calcium phenylate, aluminum isopropylate, carboxylates such as sodium formate, sodium acetate, sodium benzoate, calcium formate, calcium acetate, carbonates such as sodium carbonate, potassium carbonate, calcium carbonate, magnesium carbonate, $(NH_4)_2CO_3$, hydrogen carbonates such as NaHCO$_3$, KHCO$_3$ or NH$_4$HCO$_3$, mixtures of NH4HCO$_3$ and ammonium carbamate, ammonia, amines such as triethylamine, diethylamine, ethylamine, trimethylamine, dimethylamine, methylamine and their solutions in water or in organic solvents which are immiscible with the reaction medium. Preferably aqueous sodium hydroxide solution is used as base. If a base which forms a two-phase system with the reaction mixture is used, the organic phase containing the bisphenol indane is separated off after the neutralisation.

Following isomerisation and optional neutralisation, crude bisphenol indane is isolated from the reaction mixture. This is preferably effected by adding water to the reaction mixture and cooling and separating off the precipitate of crude bisphenol indane which forms. The quantity of water added is preferably one quarter to one third of the quantity of the reaction mixture. The reaction mixture is cooled to a temperature preferably within the range of 0 to 30° C., particularly preferably to 0 to 10° C. The reaction mixture is maintained at this temperature preferably for 1 to 200 minutes, particularly preferably for 40 to 80 minutes, before the precipitate formed is separated off. This can be effected by methods known to the person skilled in the art, for example, by filtration, decantation or centrifugation. The precipitate is then preferably washed with an organic solvent, for example, chlorobenzene.

In a preferred embodiment of the process, after being separated from the reaction mixture the precipitate is suspended in water for 5 to 100 minutes at temperatures within the range of 10 to 50° C., preferably 20 to 30° C. The quantity of water used for this is preferably one to ten times the quantity of precipitate. The precipitate is then again separated off. In a preferred embodiment, it is then washed once more at 10 to 50° C. using one to ten times the quantity of water. The solid substance obtained is dried, preferably at temperatures of 20 to 150° C., particularly preferably at 70 to 90° C. The drying is carried out preferably under reduced pressure.

The crude product is then purified by distillation under reduced pressure. Although U.S. Pat. No. 4,366,328 instructs that bisphenol indanes already undergo decomposition at temperatures from 150° C. with the formation of the corresponding indenes, with acceleration of the decomposition reaction under reduced pressure, bisphenol indane of high purity is successfully obtained in good yield from the crude product by vacuum distillation. The distillation is carried out preferably at pressures within the range of $10^{-3}$ to $10^1$ mbar and at temperatures of from 160 to 230° C., particularly preferably at $10^{-2}$ to $10^0$ mbar and 175 to 205° C.

Owing to its high purity, the bisphenol indane prepared by the process according to the invention is eminently suitable as a starting material for the production of high-grade plastics, for example, polycarbonates.

EXAMPLE 800 g dimeric isopropenylphenol was dissolved in 2000 ml chlorobenzene. The reaction mixture was heated to 80° C. and then 2.8 ml BF$_3$etherate was added. The reaction solution was heated to boiling and then maintained under reflux for 40 minutes at 132° C. The catalyst in the reaction solution was then neutralised at 80° C. by the addition of sodium hydroxide solution (1.164 g NaOH to 300 ml water). The aqueous phase was separated off, the organic phase was cooled to 0 to 10° C. and 600 ml water was added thereto. After 60 minutes the precipitate was separated off and washed with 1000 ml chlorobenzene applied in portions. 480 g product (corresponding to 60% of the initially weighed quantity of isopropenylphenol) having a bisphenol indane content of 89% was obtained.

The residue was suspended in 2000 ml water, after 15 minutes isolated again and 2000 ml water was once again added thereto in portions. The product was separated off, dried under a water-jet aspirator pump at 80° C. and then distilled at a pressure of 1 mbar. At an overhead temperature of from 195 to 198° C., 253 g (corresponding to 53% of the initially weighed crude product) of product having a bisphenol indane content of 95% was isolated.

What is claimed is:

1. A process for preparing purified 3-(4-hydroxyphenyl)-1,1,3-trimethylindan-5-ol comprising (a) isomerizing at least one member selected from the group consisting of isopropenylphenol, a dimer of isopropenylphenol and an oligomer of isopropenylphenol in a reaction mixture and in the presence of acid catalysts in an amount of 0.002 to 5 percent relative to the weight of said member, (b) isolating from the reaction mixture crude 3-(4-hydroxyphenyl)-1,1,3 trimethylindan-5-ol, and (c) purifying said crude 3-(4-hydroxyphenyl)-1,1,3-trimethylindan-5-ol by distillation under reduced pressure.

2. The process of claim 1 wherein said isomerizing is carried out in the presence of a solvent.

3. The process of claim 2 wherein solvent is 2 to 3 times the quantity of said member.

4. The process of claim 3 wherein subsequent to isomerizing the reaction mixture is neutralized by adding a base.

* * * * *